United States Patent
Tameishi (10) Patent No.: US 11,382,800 B2
(45) Date of Patent: Jul. 12, 2022

(54) METHOD OF MAKING WEARABLE ARTICLE COMPRISING ELASTIC BELT

(71) Applicant: The Procter & Gamble Company, Cincinnati, OH (US)

(72) Inventor: Kazuaki Tameishi, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 599 days.

(21) Appl. No.: 16/419,110

(22) Filed: May 22, 2019

(65) Prior Publication Data
US 2019/0274899 A1    Sep. 12, 2019

Related U.S. Application Data

(63) Continuation of application No. PCT/US2017/057829, filed on Oct. 23, 2017, which
(Continued)

(51) Int. Cl.
*A61F 13/49* (2006.01)
*A61F 13/15* (2006.01)
(Continued)

(52) U.S. Cl.
CPC .. *A61F 13/49011* (2013.01); *A61F 13/15593* (2013.01); *A61F 13/15804* (2013.01); *A61F 13/496* (2013.01); *A61F 13/49009* (2013.01); *A61F 13/49012* (2013.01); *A61F 13/49015* (2013.01); *B32B 3/04* (2013.01);
(Continued)

(58) Field of Classification Search
None
See application file for complete search history.

(56) References Cited

U.S. PATENT DOCUMENTS

| 7,901,393 B2 | 3/2011 | Matsuda et al. |
| 2004/0035521 A1* | 2/2004 | Nakakado ......... A61F 13/15593 156/229 |

(Continued)

FOREIGN PATENT DOCUMENTS

| WO | WO 2006/017718 A1 | 2/2006 |
| WO | WO 2011/087503 A1 | 7/2011 |

OTHER PUBLICATIONS

PCT International Search Report dated Jan. 4, 2018, 12 pages.

*Primary Examiner* — Barbara J Musser
(74) *Attorney, Agent, or Firm* — Charles R. Matson (57) ABSTRACT

A method of manufacturing a wearable article is disclosed. The method includes advancing a first layer of continuous sheet and a second layer of discrete continuous sheet having a smaller width than the first layer of continuous sheet; intermittently joining a first group of elastic bodies between the first layer of continuous sheet and the second layer of discrete continuous sheet; joining a second group of elastic bodies to the first layer of continuous sheets outward of the second layer of discrete continuous sheet; joining a center chassis with the first layer of continuous sheet and overlapping the first group of elastic bodies not joined to the first layer of continuous sheet; folding the first layer of continuous sheet to form a first layer fold over, wherein the first layer fold over overlaps the second group of elastic bodies, the center chassis, and the second layer of discrete continuous sheet.

19 Claims, 7 Drawing Sheets

Related U.S. Application Data is a continuation-in-part of application No. PCT/CN2016/107182, filed on Nov. 25, 2016.

(51) Int. Cl.
| | |
|---|---|
| *A61F 13/496* | (2006.01) |
| *B32B 37/14* | (2006.01) |
| *B32B 5/24* | (2006.01) |
| *B32B 43/00* | (2006.01) |
| *B32B 5/12* | (2006.01) |
| *B32B 3/04* | (2006.01) |

(52) U.S. Cl.
CPC . *B32B 5/12* (2013.01); *B32B 5/24* (2013.01); *B32B 37/144* (2013.01); *B32B 43/003* (2013.01); *Y10T 156/101* (2015.01); *Y10T 156/1011* (2015.01); *Y10T 156/1034* (2015.01); *Y10T 156/1043* (2015.01); *Y10T 156/1049* (2015.01); *Y10T 156/1051* (2015.01); *Y10T 156/1084* (2015.01)

(56) References Cited

U.S. PATENT DOCUMENTS

| | | | |
|---|---|---|---|
| 2008/0287898 A1* | 11/2008 | Guzman Reyes | ........................... A61F 13/49017 604/365 |
| 2013/0317471 A1 | 11/2013 | Morimoto et al. | |
| 2017/0143560 A1 | 5/2017 | Morimoto et al. | |

* cited by examiner

FIG. 8

METHOD OF MAKING WEARABLE ARTICLE COMPRISING ELASTIC BELT

FIELD OF THE INVENTION

The present invention relates to a method of making a wearable article comprising an elastic belt, and articles made thereof.

BACKGROUND OF THE INVENTION

Infants and other incontinent individuals wear absorbent articles such as diapers to receive and contain urine and other body exudates. Pull-on absorbent articles, or pant-type absorbent articles, are those which are donned by inserting the wearer's legs into the leg openings and sliding the article up into position about the lower torso. Pant-type absorbent articles have become popular for use on children who are able to walk and often who are toilet training, as well as for younger children who become more active in movement such that application of taped-type absorbent articles tends to be more difficult.

Belt-type pants having a main body to cover the crotch region of the wearer and a separate elastic belt defining the waist opening and leg opening are known in the art, such as described in PCT Publication WO 2006/17718A. Such belt-type pants have an elastic belt made of a laminate of 2 substrate layers and elastic bodies sandwiched therebetween. These elastic belts may be economically made by joining the elastic bodies to one of such substrate layers, overlaying and joining the other substrate layer on top to make a laminate, and then deactivating the elastic bodies in certain regions to, for example, avoid having elasticity where the elastic belt would overlap the absorbent core. While such method of making the elastic belt may be conveniently conducted by joining and deactivating all of the elastic bodies of the laminate concurrently, this may not be effective or provide the best results when different force or tactile sense is desired for different portions of the belt. Further, when the laminate is made of 2 layers of substrates, one of the layers may be folded over to avoid having sharp edges at the waist opening or the leg opening. Such a configuration results in regions that are provided in 3 layers and 2 layers. The resulting difference in layers may provide disadvantages such as non-uniform gathering to the laminate, less controllable force profile, or undesirable tactile sense. A prior publication discloses a method for assembling diaper pants using reduced material for providing the laminate elastic belt. There is interest to use as little material as possible for the elastic belt, while also assembling with the center chassis in an effective manner, and without compromise on the safety of the resulting article.

Based on the foregoing, there is a need for a method of making a wearable article comprising an elastic belt with various belt configurations without compromise on safety in an effective and economical manner.

SUMMARY OF THE INVENTION

The present invention is directed to a method of manufacturing a wearable article assembled by a front elastic belt, a back elastic belt, and a center chassis, the center chassis having a front waist region and a back waist region separated from each other by a crotch region, and having a longitudinal axis and a lateral axis; a proximal direction closer to the longitudinal center of the article and a distal direction farther from the longitudinal center of the article; the method comprising the steps of;

advancing a first layer of continuous sheet having a first surface in a machine direction, and defining a width in a cross direction;

advancing a second layer of discrete continuous sheet having a first surface in the machine direction, the second layer of discrete continuous sheet being a repetition of discrete sheets discontinuous in the machine direction having a smaller width than the first layer of continuous sheet;

advancing a first group of elastic bodies in the machine direction in a stretched state, wherein all of the first group of elastic bodies are intermittently directly joined to the first surface of the first layer of continuous sheet and the first surface of the second layer of discrete continuous sheet;

directly joining the first surface of the first layer of continuous sheet and the first surface of the second layer of discrete continuous sheet;

advancing a second group of elastic bodies in the machine direction in a stretched state, wherein the second group of elastic bodies are directly joined to the first surface of the first layer of continuous sheets in regions outward of the second layer of discrete continuous sheet in the width direction;

directly joining the center chassis with the first layer of continuous sheet overlapping the regions in which the first group of elastic bodies are not directly joined to the first surface of the first layer of continuous sheets;

folding the first layer of continuous sheet to form a first layer fold over of continuous sheet, and directly joining the first layer of continuous sheet and the first layer fold over of continuous sheet, wherein the first layer fold over of continuous sheet overlaps all of the second group of elastic bodies and at least partially overlaps the center chassis and the second layer of discrete continuous sheet.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DEFINITIONS

As used herein, the following terms shall have the meaning specified thereafter:

"Wearable article" refers to articles of wear which may be in the form of pants, taped diapers, incontinent briefs, feminine hygiene garments, and the like. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants".

"Longitudinal" refers to a direction running substantially perpendicular from a waist edge to an opposing waist edge of the article and generally parallel to the maximum linear dimension of the article. "Transverse" refers to a direction perpendicular to the longitudinal direction.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the present article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element. Joining may be provided by applying adhesive agents, ultrasound, pressure, heat, or the combination thereof.

"Proximal" refers to a portion being closer or planned to be closer relative to the longitudinal center of the article, while "distal" refers to a portion being farther or planned to be farther from the longitudinal center of the article.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Extendibility" and "extensible" mean that the width or length of the component in a relaxed state can be extended or increased.

"Elasticated" and "elasticized" mean that a component comprises at least a portion made of elastic material.

"Elongatable material", "extensible material", or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

DETAILED DESCRIPTION OF THE INVENTION

Figure 1:
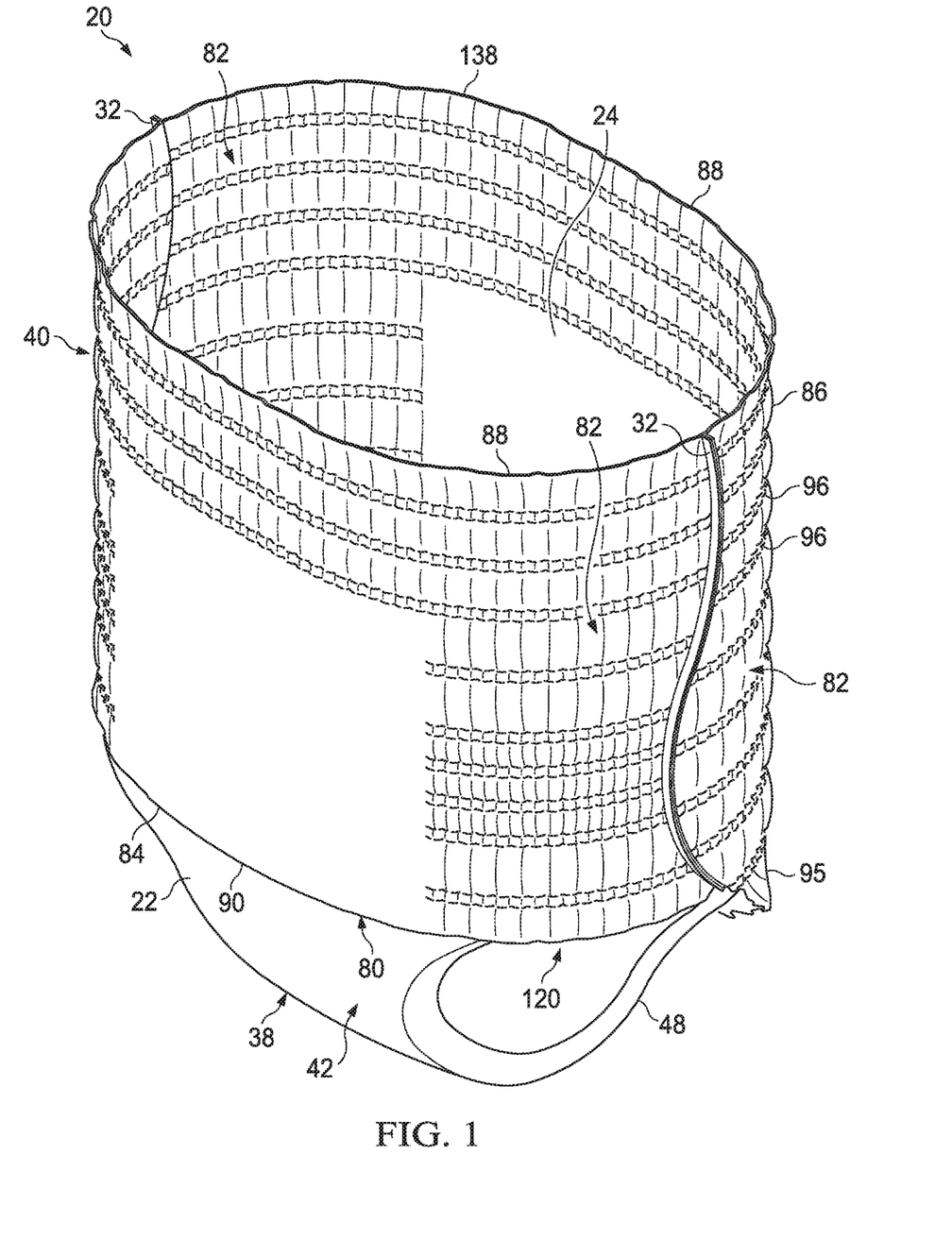
FIG. 1 is a perspective view of one embodiment of a wearable article of the present invention.
Figure 2:
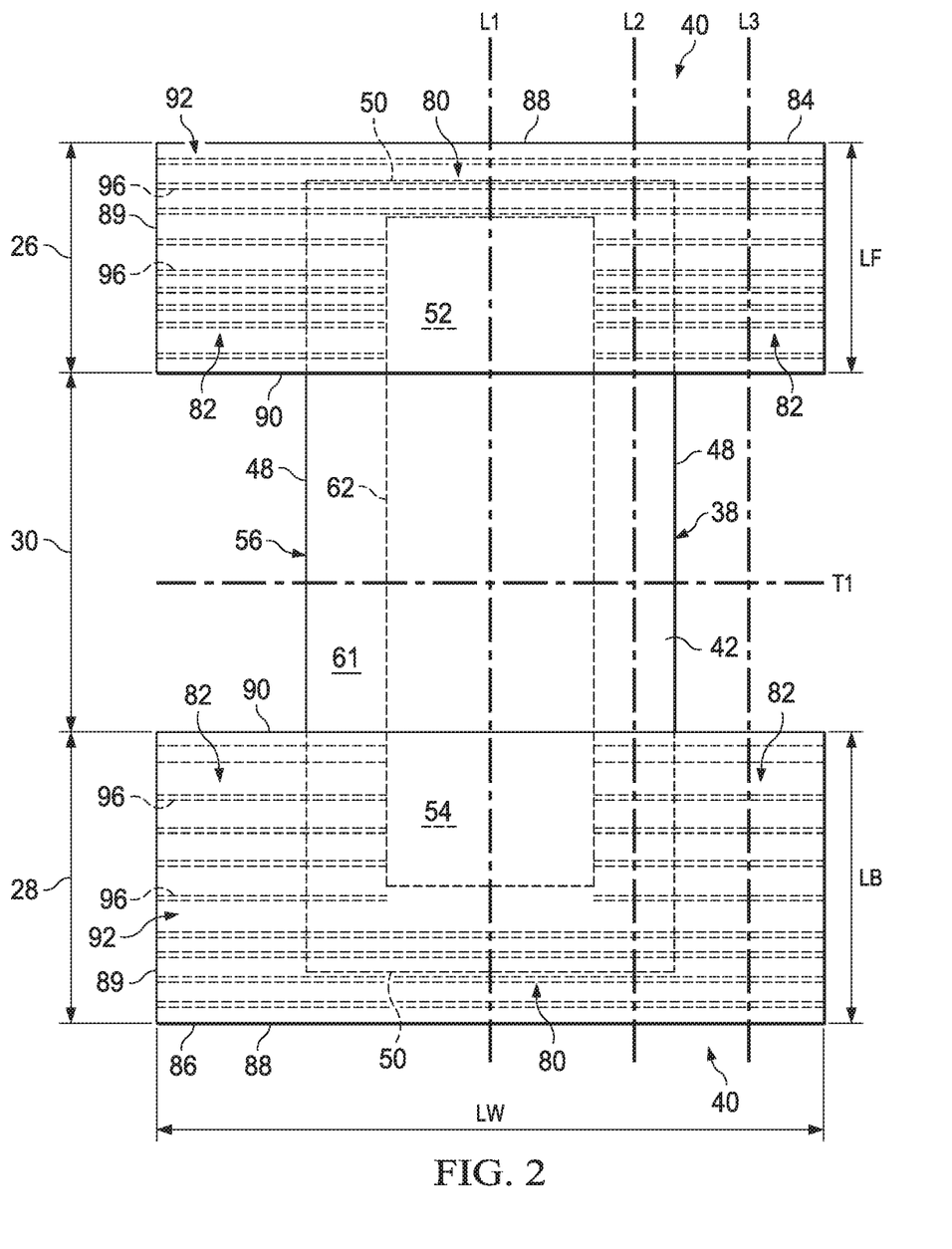
FIG. 2 is a schematic plan view of one embodiment of a wearable article of the present invention with the seams enjoined and in a flat uncontracted condition showing the garment facing surface.

FIG. 1 is a perspective view of an embodiment of the wearable article 20 made by the present invention and FIG. 2 is a schematic plan view of the same article with the seams unjoined and in its flat uncontracted condition showing the garment-facing surface. In FIGS. 1 and 2, the position of the elastics 96 may or may not be accurate. The wearable article 20 has a longitudinal centerline L1 which also serves as the longitudinal axis, and a transverse centerline T1 which also serves as the transverse axis. The wearable article 20 has a body facing surface, a garment facing surface, a front region 26, a back region 28, a crotch region 30, and seams 32 which join the front region 26 and the back region 28 to form two leg openings and a waist opening. The wearable article 20 comprises a center chassis 38 to cover the crotch region of the wearer, a front elastic belt 84 and a back elastic belt 86 (hereinafter may be referred to as "front and back elastic belts"), the front and back elastic belts 84, 86 forming a ring-like elastic belt 40 (hereinafter may be referred to as "waist belt") extending transversely defining the waist opening. The front and back elastic belts 84, 86 and the center chassis 38 jointly define the leg openings.

Figures 3A, 3B:
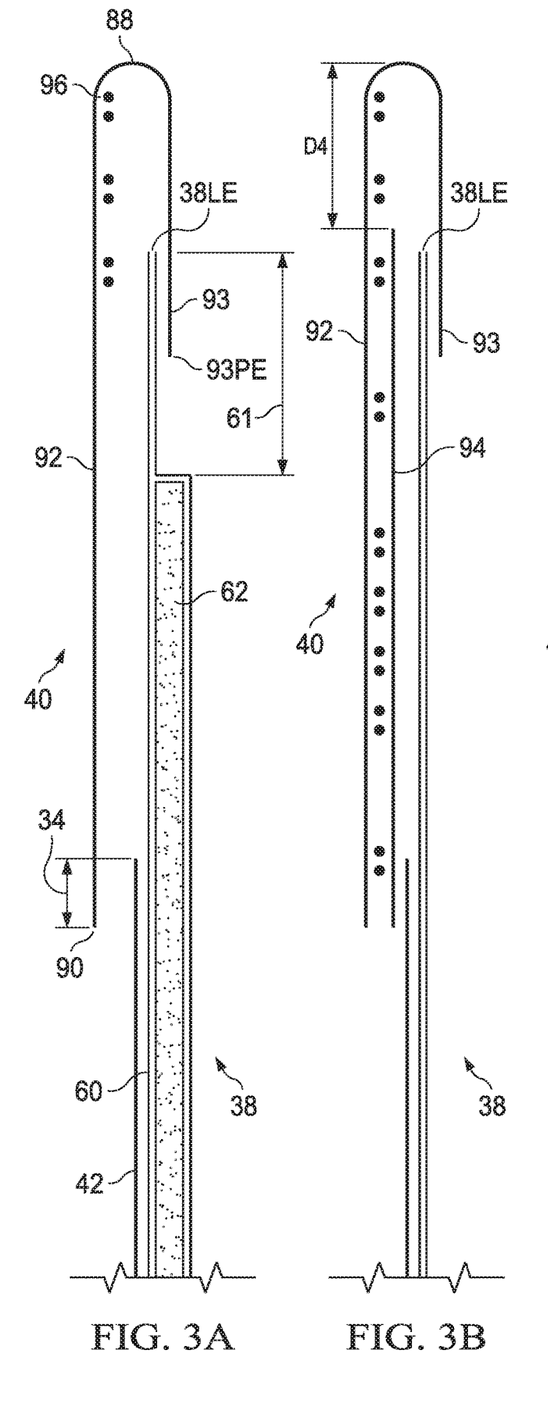
FIG. 3A is a schematic cross section view of FIG. 2 taken along line L1 in one embodiment of belt structure, either on the front elastic belt or the back elastic belt.
FIG. 3B is a schematic cross section view of FIG. 2 taken along line L2 in one embodiment of belt structure, either on the front elastic belt or the back elastic belt.
Figures 3C, 4:
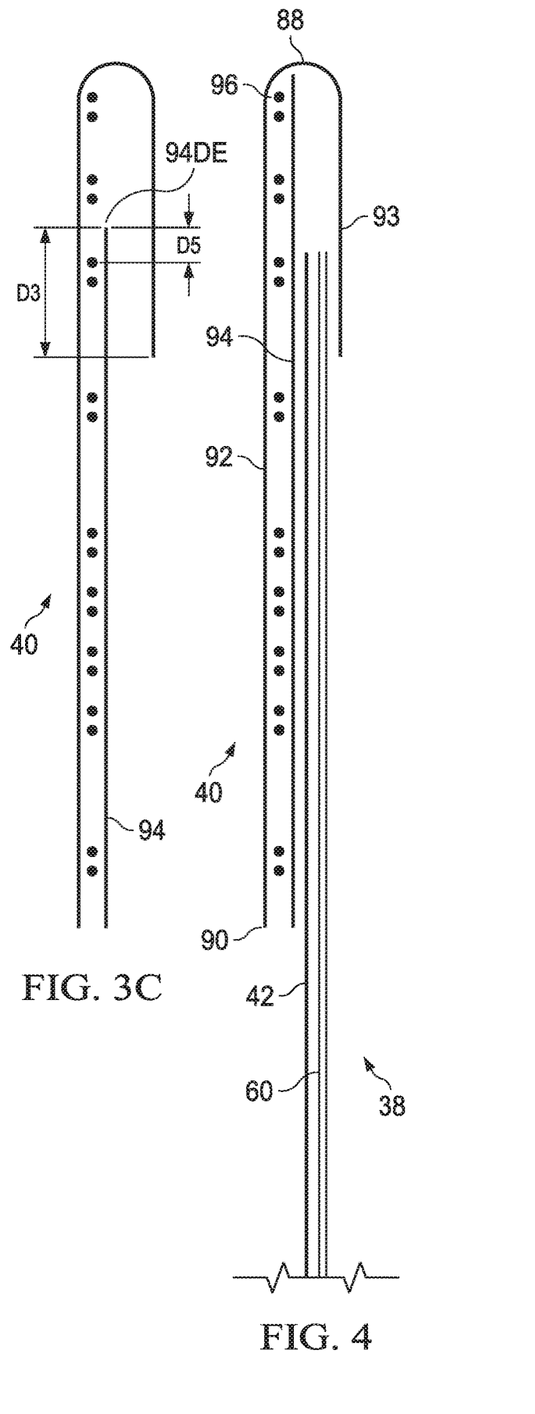
FIG. 3C is a schematic cross section view of FIG. 2 taken along line L3 in one embodiment of belt structure, either on the front elastic belt or the back elastic belt.
FIG. 4 is a schematic cross section view of a wearable article of the prior art taken along the analogous of line L2 in a belt structure.

FIGS. 3A, 3B, and 3C are schematic cross section views of one embodiment article made by the present invention, taken along lines L1, L2, and L3, respectively. L1 describes the longitudinal centerline, while L2 describes a longitudinal line running through the transverse edge of the center chassis 38, and L3 describes a longitudinal line running through the left and right panels 82 where the center chassis 38 does not exist. FIG. 4 is a schematic cross section view of the prior art taken along the analogous line of L2 of a belt-type pant article. In FIGS. 3A-3C, and 4, the thickness dimension may be exploded and exaggerated.

Referring to FIG. 3A, the center chassis 38 comprises a backsheet 60 and outer cover layer 42 for covering the garment-facing side of the backsheet 60. The backsheet 60 may be a water impermeable film. The outer cover layer 42 may be a nonwoven sheet. The center chassis 38 may contain an absorbent material existing region 62 for absorbing and containing body exudates disposed on the center chassis 38, and an absorbent material non-existing region 61 surrounding the periphery of the absorbent material existing region 62. In the embodiment shown in FIG. 2, the center chassis 38 has a generally rectangular shape, left and right longitudinally extending side edges 48 (hereinafter may be referred to as "side edge") and front and back transversely extending end edges 50 (hereinafter may be referred to as "end edge"). The center chassis 38 also has a front waist panel 52 positioned in the front region 26 of the wearable article 20, a back waist panel 54 positioned in the back region 28, and a crotch panel 56 between the front and back waist panels 52, 54 in the crotch region 30. The center of the front elastic belt 84 is joined to a front waist panel 52 of the center chassis 38, the center of the back elastic belt 86 is joined to a back waist panel 54 of the center chassis 38, the front and back elastic belts 84, 86 each having a left side panel and a right side panel 82 where the center chassis 38 does not overlap. The center chassis has a crotch panel 56 positioned between the front waist panel 52 and the back waist panel 54. The front and back elastic belt are discontinuous of each other in the longitudinal direction.

Referring to FIGS. 1 and 2, the ring-like belt 40 formed by the front elastic belt 84 and back elastic belt 86 acts to dynamically create fitment forces and to distribute the forces dynamically generated during wear. The front and back elastic belts 84, 86 may be joined with each other only at the side edges 89 at the seams 32 to form a wearable article having a waist opening and two leg openings. Each leg opening may be provided with elasticity around the perimeter of the leg opening by the combination of elasticity from the front elastic belt 84, the back elastic belt 86, and any from the center chassis 38. The front leg opening region 120 is disposed adjacent the leg opening along the proximal edge 90 of the left and right side panels 82 of the front elastic belt 84.

The front elastic belt 84 and back elastic belt 86 are configured to impart elasticity to the belt 40. The front elastic belt 84 and the back elastic belt 86 may each be formed by a laminate comprising a plurality of elastic bodies 96 running in the transverse direction, an inner sheet 94, an outer sheet 92, and an outer sheet fold over 93 wherein the outer sheet fold over 93 is an extension of the outer sheet material formed by folding the outer sheet material at the distal edge 88 of the front and back elastic belts; wherein the belt elastic bodies 96 are sandwiched between two of these sheets. The front elastic belt 84 and the back elastic belt 86 may each be made only by elastic bodies 96, the inner sheet 94, the outer sheet 92, and the outer sheet fold over 93. The outer sheet fold over 93 may be directly joined to the center chassis 38. The belt elastic bodies 96 may extend in the transverse direction to provide a ring like elastic belt 40 when the front elastic belt 84 and the back elastic belt 86 are joined. At least some of the elastic bodies 96 extend in the transverse direction substantially parallel to each other. All of the elastic bodies 96 may extend in the transverse direction substantially parallel to each other. Such an article may be economically made. The front and back elastic belt 84, 86 each have transversely continuous proximal and distal edges, the proximal edge 90 being located closer than the distal edge 88 relative to the longitudinal center of the article. The outer sheet fold over 93 is an extension of the outer sheet material formed by folding the outer sheet material at the distal edge 88 of the front and back elastic belts 84, 86. The elastic bodies 96 may be disposed in the same or different denier, interval, or force between the front and back, as well as in different longitudinal positions of the belt. The inner and outer sheets 92, 94 may be the same or different material, and selected to provide characteristics such as breathability, softness, cushiony feel, loftiness, and combinations thereof, depending on the desirables of the resulting article. The inner and outer sheets 92, 94 may have the same or different basis weight, stiffness, texture or any combination thereof.

Referring to FIG. 2, the transverse width LW of the back elastic belt 86 in the uncontracted condition may be the same as the transverse width of the front elastic belt 84 of the same condition. Such an article may be economically made.

The longitudinal length LB of the back elastic belt 86 between the back distal edge 88 and the back proximal edge 90 along its entire width LW of the back elastic belt 86 may be approximately the same as the longitudinal length LF of the front elastic belt 84 between the front distal edge 88 and the front proximal edge 90. In such configuration, the seams 32 close the front and back elastic belt 84, 86 side edges 89 of the same length for forming the article. Such an article may be economically made.

The back elastic belt 86 may have a greater longitudinal length LB between the back distal edge 88 and the back proximal edge 90 along its entire width LW of the back elastic belt 86 in the transverse direction than the longitudinal length LF of the front elastic belt 84 between the front distal edge 88 and the front proximal edge 90 (FIGS. 1 and 2). In such configuration, when the wearable article is assembled to form the waist opening and the leg openings, the wearable article 20 is folded along the transverse centerline T1 such that the front distal edge 88 is aligned with the back distal edge 88. The front side edge 89 is also aligned with a portion of the back side edge 89. Then the front elastic belt 84 and the back elastic belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the center chassis 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1.

Referring to FIGS. 2 and 3A-3C, the front and back elastic belts 84, 86 are discontinuous with one another in the crotch region 30, and therefore the outer cover layer 42 is the garment-facing surface in the crotch region 30. The outer cover layer 42 may extend only partly in the longitudinal direction of the front waist panel 52 and/or the back waist panel 54 to leave the distal parts of the front waist panel 52 and the back waist panel 54 free of the outer cover layer 42. Namely, the longitudinal length of the outer cover layer 42 may be longer than the longitudinal length of the crotch panel 56 and shorter than the longitudinal length of the backsheet 60. By such configuration, the distal parts of the front waist panel 52 and the back waist panel 54 are devoid of the outer cover layer 42, providing better breathability to the overall article. Further, this may provide cost saving of the outer cover layer 42 material. Accordingly, looking at the difference in layers of elements between the garment facing surface and the backsheet of the center chassis 38 of FIG. 3A-3B compared to FIG. 4, there exists a transitional region 34 disposed on the waist panel 52 where the outer cover layer 42 is present. The longitudinal length of the transitional region 34 may be made as short as possible, for example, less than about 20 mm, or less than about 15 mm, or less than about 10 mm. Further, adhesive may be applied on the entire area of the transitional region 34, or the entire area leaving no more than up to 5 mm, in the longitudinal direction, from the distal edge of the transitional region 34. For providing attractive artwork for a wearable article in an economical manner, it is common practice to provide printing on the garment facing side of the backsheet 60. By providing the transitional region 34 as short as possible, applying adhesive to enhance transparency, or simply avoiding displaying artwork in this region, compromised appearance of the artwork over different layers of material between the artwork and the observer may be avoided.

Articles known in the art such as in FIG. 4 have the longitudinal length of the inner sheet approximately matching the longitudinal length of the elastic belt. This provides regions of the elastic belt having 3 layers for a significant percentage of the belt while leaving the other regions in 2 layers.

Referring to FIGS. 3A-3C, the present invention enables manufacturing of articles having a region towards the distal edge of the elastic belt 88 wherein the elastic belt 40 is made only by the outer belt 92, the outer belt fold over 93, and elastics 96 disposed therebetween. In FIGS. 3B-3C, there are 4 elastic bodies 96 which are disposed between the outer belt 92 and the outer belt fold over 93, 2 elastic bodies 96 which are disposed where 3 layers overlap (outer belt 92, inner belt 94, and outer belt fold over 93), and 12 elastic bodies 96 which are disposed between the inner belt 94 and the outer belt 92. Namely, a majority of elastic bodies are disposed between 2 layers.

Figure 6:
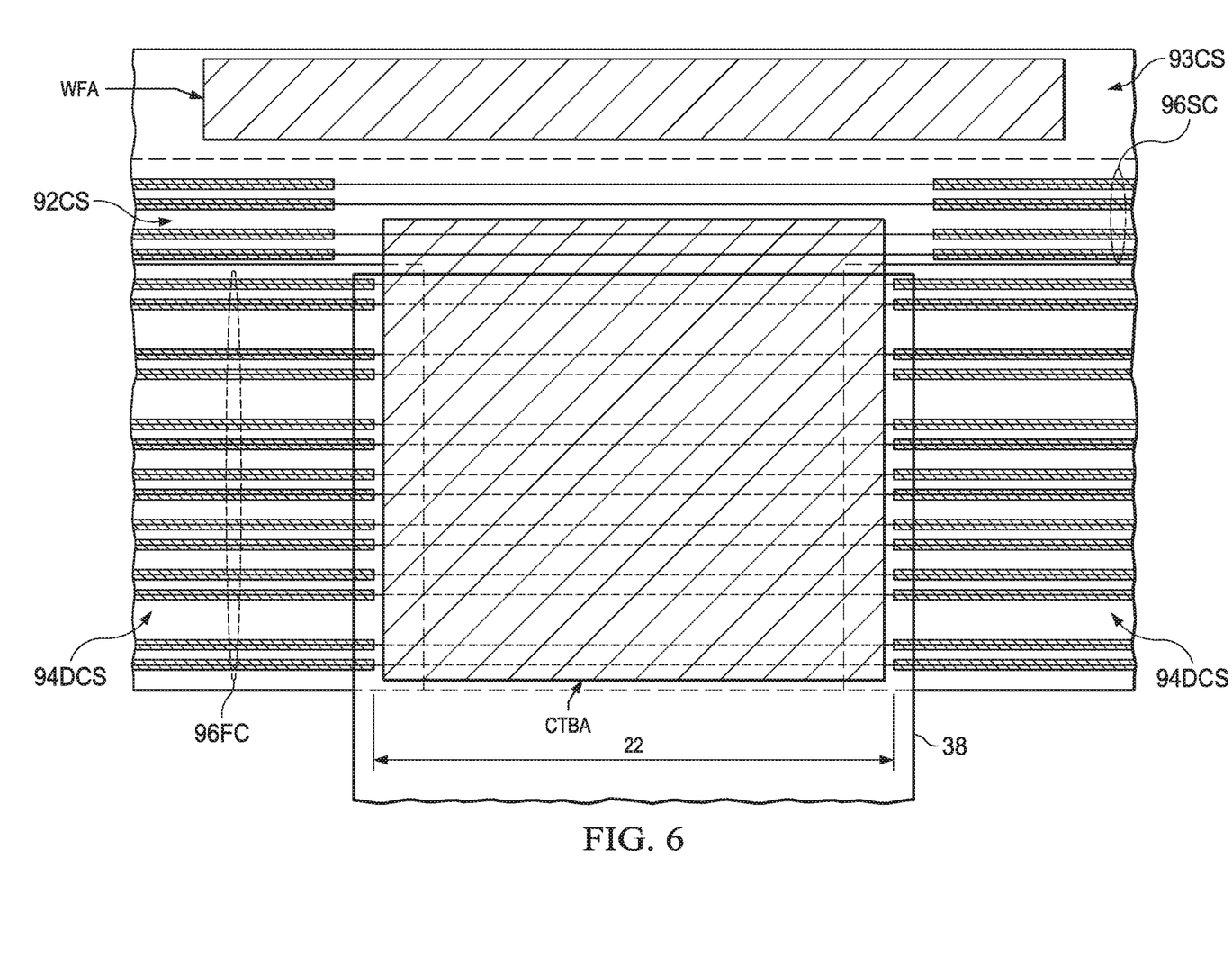
FIG. 6 is a schematic view showing an embodiment of how the parts are joined with each other showing the body-facing surface.

Referring to FIGS. 2, 3A and 6, the present invention further enables manufacturing of articles having front and back waist panels 52, 54 which are devoid of the inner belt 94 over a significant percentage of area. Namely, the inner belt 94 is joined with the outer belt 92 in areas where the center chassis 38 does not exist, however, is removed in a significant percentage of area where the center chassis 38 overlaps. Such configuration provides significant savings for the inner belt 94 material, while maintaining enough structural rigidity for the front waist panel 52 and/or a back waist panel 54, in that this area is overlapped by the center chassis 38. The present invention further enables such manufacturing without compromise on safety in an effective and economical manner, as described in detail below. What is meant by safety is, absence of undesirable material touching the wearer's skin, or escaping the wearable article. Undesirable material include, for example, excessive adhesive material which may negatively affect the wearer's skin, uncovered elastic bodies which may negatively affect the wearer's skin, and elastic body fragments which may be a choking hazard if escaped from the wearable article during usage.

Figure 5:
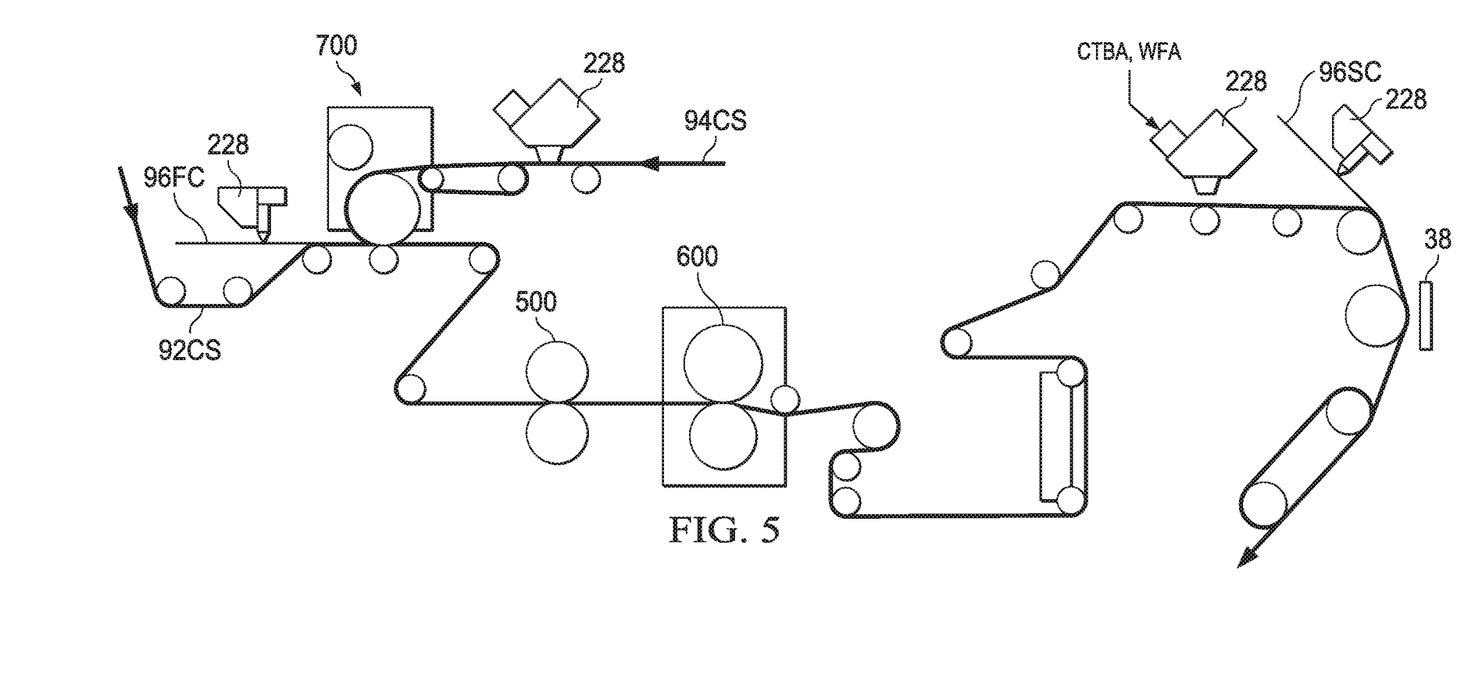
FIG. 5 is a schematic view of the process of the present invention.

FIG. 5 is a schematic view of the entirety of the process of the present invention comprising the following steps A)-D).

A) Related to introducing a first group of elastic bodies 96FC, the step comprising:
advancing a first layer of continuous sheet 92CS having a first surface in a machine direction and defining a width in a cross machine direction;
advancing a second layer of discrete continuous sheet 94DCS having a first surface in the machine direction and having a smaller width than the first layer of continuous sheet;
advancing a first group of elastic bodies 96FC in the machine direction in a stretched state wherein all of the first group of elastic bodies are intermittently directly joined to the first surface of the first layer of continuous sheet 92CS and the first surface of the second layer discrete continuous sheet 94DCS; and
directly joining the first surface of the first layer of continuous sheets 92CS and the first surface of the second layer of discrete continuous sheet 94DCS.

B) Related to introducing a second group of elastic bodies 96SC comprising:
advancing a second group of elastic bodies 96SC in the machine direction in a stretched state; wherein the second group of elastic bodies 96SC are directly joined to the first surface of the first layer of continuous sheet 92CS in regions outward of the second layer of discrete continuous sheet 94DCS in the width direction.

C) Related to joining the center chassis 38 to the first surface of the first layer of continuous sheet 92CS comprising:
directly joining the center chassis 38 with the first layer of continuous sheet 92CS overlapping the regions in which the first group of elastic bodies 96FC are not directly joined to the first surface of the first layer continuous sheet 92CS.

D) Related to folding the first layer of continuous sheet to form a first layer fold over of continuous sheet 93CS, and directly joining the first layer of continuous sheet 92CS and the first layer fold over of continuous sheet 93CS, wherein the first layer fold over of continuous sheet 93CS overlaps all of the second group of elastic bodies 96SC and at least partially overlaps the center chassis 38 and the second layer of discrete continuous sheet 94DCS.

In the finished article, the first layer of continuous sheet 92CS becomes the outer sheet 92 wherein the second surface of the first layer of continuous sheet 92CS becomes the garment-facing surface of the article, the second layer of discontinuous continuous sheet 94DCS becomes the inner sheet 94 wherein the second surface of the second layer of discrete continuous sheet 94DCS becomes the body-facing surface of the article, and the first layer fold over of continuous sheet 93CS becomes the outer sheet fold over 93 wherein the second surface of the first layer fold over of continuous sheet 93CS becomes the body-facing surface of the article.

FIG. 6 is a schematic view of the positioning of material parts and joining regions of the process of the present invention featuring one belt of one article. The configurations of parts and joining regions of the present invention are discussed in detail below.

Step A)

Figure 7:
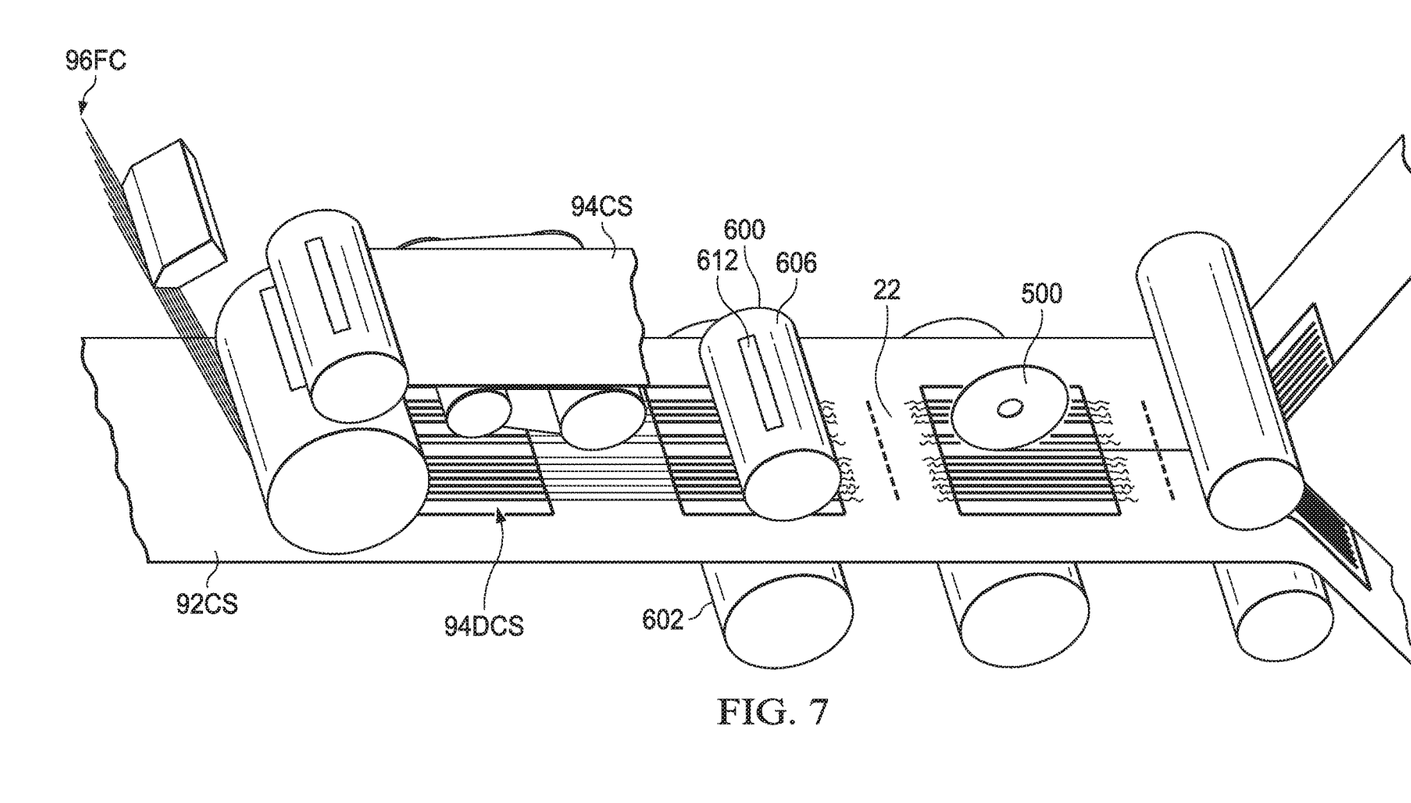
FIG. 7 is a schematic view of the primary elastic belt precursor forming step of the process of the present invention.

Referring to FIGS. 5, 6, and 7, the first elastic introduction step comprises advancing a first layer of continuous sheet 92CS having a first surface and an opposing second surface in a machine direction; advancing a second layer of discrete continuous sheet 94DCS having a first surface and an opposing second surface in the machine direction; advancing a first group of elastic bodies 96FC in the machine direction in a stretched state; and joining all of the first group of elastic bodies 96FC between the first surface of the first layer of continuous sheet 92CS and the first surface of the second layer of discrete continuous sheet 94DCS. Referring to FIG. 7, what is meant by discrete continuous sheet is that the sheet is a repetition of discrete sheets having the same continuous dimension in the cross machine direction, however being discontinuous in the machine direction in a predetermined interval. Referring to FIG. 5, the second layer of continuous sheet 94CS is processed through a cut and slip equipment 700 prior to joining with the first layer of continuous sheet 92CS.

In FIG. 7 the first group of elastic bodies 96FC are placed in the center in the cross machine direction of the first layer of continuous sheet 92CS on the proviso that the assembly will later be divided into 2 continuous belt precursor parts for making the front elastic belt 84 and the back elastic belt 86. In FIG. 7, the depiction after joining of the second layer of discrete continuous sheet 94DCS is shown as if the second layer of discrete continuous sheet 94DCS is removed and therefore the elastic bodies can be directly observed. The first layer of continuous sheet 92CS and second layer of discrete continuous sheet 94DCS have a width in a cross machine direction; wherein the second layer of discrete continuous sheet 94DCS has a smaller width than the first layer of continuous sheet 92CS to enable introducing the second group of elastic bodies 96SC in the later steps. Referring to FIGS. 3B-3C, the dimension of the second layer of discrete continuous sheet 94DCS and the positioning of first group of elastic bodies 96FC may be selected such that the elastic body closest to the edge of the second layer of discrete continuous sheet 94DCS is disposed at a distance D5 away from the edge of second layer of discrete continuous sheet 94DCS, wherein D5 may be at least about 5 mm. This may prevent any elastic body 96 from being accidentally left uncovered by the inner sheet 94 in the finished article. The first group of elastic bodies 96FC may be joined between the first and second layers of (discrete) continuous sheets 92CS, 94DCS by any means known in the art, such as applying adhesive material by adhesive dispensers 228 immediately before joining.

Referring to FIG. 6, all of the first group of elastic bodies 96FC are intermittently directly joined to the first surface of the first layer of continuous sheet 92CS such that at least the directly joined regions are overlayed with the second layer of discrete continuous sheet 94DCS. On the other hand, at least a portion of the regions where the first group of elastic bodies 96FC are not joined to the first layer of continuous sheet 92CS; are not overlayed by the second layer of discrete continuous sheet 94DCS. Thus, some discrete repeating parts of the first group of elastic bodies 96FC are left stretched and unattached to any substrate. These discrete repeating parts of the first group of elastic bodies 96FC are uncovered by the second layer of discrete continuous sheet 94DCS, thus are provided absent of adhesive material while the assembly is delivered to the next step. The unattached portions may also provide cost savings of adhesive material. These discrete repeating parts of the first group of elastic bodies 96FC which are left stretched and unattached to any substrate; may later form a non-elastic region 22 discussed below.

Meanwhile, the first surface of the first layer of continuous sheets 92CS and the first surface of the second layer of discrete continuous sheet 94DCS are directly joined to each other. The region in which the first layer of continuous sheets 92CS and the first surface of the second layer of discrete continuous sheet 94DCS are directly joined to each other may be selected according to the desirables of the resulting article. The first layer of continuous sheet 92CS and the second layer of discrete continuous sheet 94DCS may be directly joined along the periphery of the region which is planned to become the proximal edge 90 of the front elastic belt 84 or the back elastic belt 86. This ensures that any elastic bodies sandwiched between the first layer of continuous sheets 92CS and the first surface of the second layer of discrete continuous sheet 94DCS are not accidentally left unjoined along the leg opening.

Up to this step, the parts may be joined directly with each other by applying adhesive material by adhesive dispensers 228 immediately before joining such parts as in FIG. 7. Alternatively, the parts may be placed in predetermined position, and then sent to an ultrasonic, thermal, or pressure application station for joining certain of the parts in such predetermined position (not shown).

Referring to FIG. 7, the obtained assembly may be divided by a slitter 500 in the machine direction to form 2 continuous parts, which are the front elastic belt precursor and the back elastic belt precursor. The dividing may be provided before or after optional making of a non-elastic region 22 as described below. The front elastic belt precursor and the back elastic belt precursor may be different in at least one of; the dimension of the precursor, the number of first group of elastic bodies, and the positioning of the first group of elastic bodies.

The thus obtained assembly comprising: the lamination of the first layer of continuous sheet 92CS, the second layer of discrete continuous sheet 94DCS and first group of elastic bodies 96FC; may comprise an elastic region and a non-elastic region 22. By elastic region, what is meant is a region which contributes to the elasticity of the waist belt 40 in the final article. By non-elastic region 22, what is meant is a region which does not contribute to the elasticity of the waist belt 40 in the final article. An elastic body unadhered to the first and second layers of (discrete) continuous sheets 92CS, 94DCS and cut in the unadhered area may be left dangling, thereby still exhibiting elasticity as an elastic body per se. However, so long as the elasticity is non-contributory to elasticity of the waist belt 40, such area is considered a non-elastic region 22. On the other hand, an elastic body unadhered to either or both of the first and second layers of (discrete) continuous sheets 92CS, 94DCS while continuing to exhibit elasticity is considered active in elasticity. Such area is considered an elastic region. At least one of the first group of elastic bodies 96FC may be removed of its elasticity in regions planned to be joined to the transverse center of the center chassis 38, namely to provide a non-elastic region 22. Removal of elasticity from a certain area of the elastic belt 40 overlapping with the corresponding front and/or back waist panel 52, 54 may be advantageous when the center chassis 38 comprises an absorbent material existing region 62, in that elasticity in the front and/or back waist panel 52, 54 may cause bunching of the absorbent material existing region 62 and interfere with close fit of the center chassis 38 to the wearer.

The elasticity of at least one of the first group of elastic bodies 96FC may be removed by leaving the elastic body unadhered to the first and second layers of continuous sheets 92CS, 94CS over the planned dimension of the non-elastic region 22, and then deactivating the elastic bodies disposed in the intermittently unadhered portion. A cutting unit may be employed for effective deactivation, and may be configured with a die knife, flexible blade, and/or compression roll features, and may also include additional features to control knife-anvil gaps and/or force, and may include means for heating. The cutting unit may include a cutting roll 600, an anvil roll 602, and a flexible blade 612 extending from the roll circumference surface 606 of the cutting roll 600.

Referring to FIG. 6, the first group of elastic bodies 96FC joined under the center chassis 38 are depicted as if remaining in active elasticity, however, this is not intended to be limiting of the present invention. All of the first group of elastic bodies 96FC may be deactivated. Only one, or a portion of the first group of elastic bodies 96FC may be deactivated, for example, those that are planned to be disposed closer to the proximal edge 90 of the resulting article. Accordingly, the at least one of, or some of the first group of elastic bodies 96FC may not be deactivated and thus remain in active elasticity across the planned width of the elastic belt 40. The dimension of the non-elastic region 22 may be determined by the enjoined length of the first group of elastic bodies 96FC in the machine direction. The dimension of the non-elastic region 22 may be the same for multiple elastic bodies, or varied per elastic body.

Step B)

Referring to FIGS. 5 and 6, the thus obtained assembly is then joined with the second group of elastic bodies 96SC comprising the steps of: advancing a second group of elastic bodies 96SC in the machine direction in a stretched state, wherein the second group of elastic bodies 96SC are joined to the first surface of the first layer of continuous sheets 92CS in regions outward of the second layer of discrete continuous sheet 94DCS in the width direction. The second group of elastic bodies 96SC may be intermittently directly joined to the first surface of the first layer of continuous sheets 92CS, leaving some discrete repeating parts of the second group of elastic bodies 96SC left stretched and unattached to any substrate. These unattached portions of the second group of elastic bodies 96SC may not be deactivated. The unattached portions of the second group of elastic bodies 96SC may be kept actively elastic by joining between the first surface of the first layer of continuous sheet 92CS and the first surface of the first layer fold over of continuous sheet 93CS by adhesive in the following steps. The unattached portions may provide cost savings of adhesive material.

Step C)

Referring to FIGS. 5 and 6, the thus obtained assembly is then joined with the center chassis 38. Referring to FIG. 6, the center chassis 38 is directly joined with the first surface of the first layer of continuous sheet 92CS overlapping the regions where the first group of elastic bodies 96FC are not directly joined to the first surface of the first layer of continuous sheets 92CS. Namely, the center chassis 38 overlays at least the region where the second layer of discrete continuous sheet 94DCS does not exist, and further overlap the second layer of discrete continuous sheet 94DCS in the machine direction by at least about 5 mm. This ensures that any accidentally fragmented elastic body is covered by the center chassis 38, thus preventing it from escaping the article from the leg opening. Fragmented elastic bodies may be unintentionally created during the above mentioned optional deactivating step of the first group of continuous elastic bodies 96FC. The second layer of discrete continuous sheet 94DCS may be planned to have about the same, or narrower, or wider dimension in the cross machine direction than that of the center chassis 38, so long as all of the first group of elastic bodies 96FC are covered by one or both of the second layer of discrete continuous sheet 94DCS and the center chassis 38. The joining of the center chassis 38 may be provided by applying a chassis-to-belt adhesive CTBA where the center chassis 38 is planned to be positioned. The chassis-to-belt adhesive CTBA may be applied beyond the width of the center chassis 38 in the cross machine direction. By applying the chassis-to-belt adhesive CTBA in such dimension, undesired foldover of the edge of the center chassis 38 may be avoided. When the second layer of discrete continuous sheet 94DCS has a wider dimension in the cross machine direction than that of the center chassis 38, the chassis-to-belt adhesive CTBA may further be applied beyond the width of the second layer of discrete continuous sheet 94DCS in the cross machine direction. By applying the chassis-to-belt adhesive CTBA in such dimension, undesired foldover of the edge of the second layer of discrete continuous sheet 94DCS may be avoided. The chassis-to-belt adhesive CTBA may be applied in a dimension shorter than the length of the center chassis 38 in the machine direction. By applying the chassis-to-belt adhesive CTBA in such dimension, exposure of glue on the body-facing surface, which may eventually touch the wearer, may be avoided. When observed from the body-facing surface, the chassis-to-belt adhesive CTBA exists under the center chassis 38, however, in FIG. 6 such portion of the chassis-to-belt adhesive CTBA is depicted as if the center chassis 38 is removed and therefore the chassis-to-belt adhesive CTBA may be directly observed.

Figure 8:
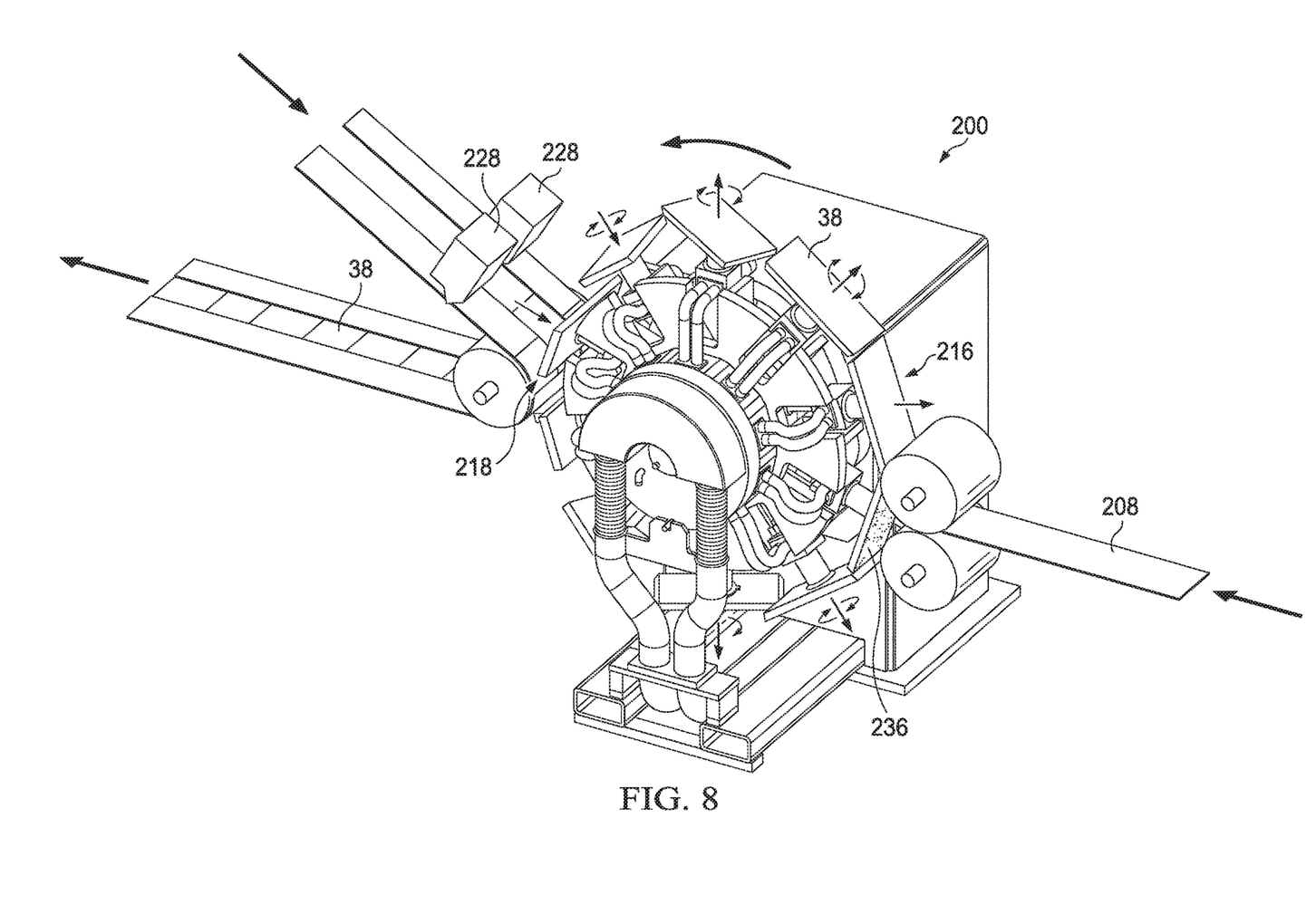
FIG. 8 is a schematic view of the center chassis forming and joining step of the process of the present invention.

Preceding this step, referring to FIG. 8, the center chassis 38 may be formed by cutting a continuous center chassis 208 into discrete pieces, and processing through a transfer assembly 200. The transfer surface 236 of the transfer assembly 200 may pick up the center chassis 38 in a first position 216, turn the transfer surface 236 together with the center chassis 38 into a second position 218 while spacing the center chassis 38 as appropriate, and transferred to be joined; such that the transverse axis of the center chassis 38 is aligned with the machine direction of the elastic belt making assembly. During the turning, the center chassis 38 may be held by the transfer surface 236 via vacuum. Upon transferring of the center chassis 38 from the transfer surface 236 to the assembly, vaccum is released, and instead the center chassis 38 is pressed onto the assembly for securely joining. When the cross machine width of the center chassis 38 (the longitudinal length of the center chassis 38 in the resulting article) matches that of the transfer surface 236, the chassis-to-belt adhesive CTBA may exist beyond the width of the center chassis 38 in the cross machine direction, as in FIG. 6. This ensures attachment of the edges of the center chassis 38 until it is covered by the first layer folder over of continuous sheets 93CS, in the next step. While it is ideal to match the planar dimension of the transfer surface 236 and the center chassis 38, this may not always be possible for economic reasons. As such, the transfer surface 236 may be slightly greater in dimension compared to the center chassis 38. When the transfer surface 236 is greater in dimension compared to the center chassis 38, care is taken such that unnecessary material, such as adhesive material, does not transfer from the assembly to the transfer surface 236 upon joining the center chassis 38. For example, any portion of the second group of elastic bodies 96SC which may contact the transfer surface 236 may be absent of adhesive material to avoid transfer of adhesive material to the transfer surface 236. In another example, the region in which the chassis-to-belt adhesive CTBA is applied may be adjusted so as not to contact the transfer surface 236.

Step D)

Still referring to FIGS. 5 and 6, the obtained assembly is then sent to folding the first layer to form a first layer fold over of continuous sheet 93CS, such that the second group of elastic bodies 96SC are directly joined between the first surface of the first layer of continuous sheets 92CS and the first surface of the first layer fold over of continuous sheets 93CS.

Referring to FIGS. 3B-3C and 6, the first layer fold over of continuous sheet 93CS overlaps all of the second group of elastic bodies 96SC, and may further partially overlap the center chassis 38 and the second surface of the second layer of discrete continuous sheet 94DCS. By taking such configuration, the resulting article has the center chassis 38 securely sandwiched by at least the inner sheet 94 and the outer sheet fold over 93 in the vicinity of the longitudinal edge 38LE by having an overlap D3 with the outer sheet fold over 93 in the longtitudinal direction, wherein D3 may be from about 10 mm to about 50 mm, or from about 10 mm to about 45 mm. Referring to FIGS. 3B-3C, in the resulting article, the inner sheet 94, however, does not extend to the distal edge 88 of the belt, thus, leaving some region where the belt is configured only by the outer sheet 92 and the outer sheet fold over 93. The inner belt distal edge 94DE may have a distance D4 from the belt distal edge 88, wherein D4 may be from about 10 mm to about 90 mm. By having such distance, meaningful cost saving of the inner sheet 94 is provided, while maintaining overall rigidity for the article. There may be at least 2 second group of elastic bodies 96SC, or from about 2 to about 8 second group of elastic bodies 96SC, or from about 2 to about 6 second group of elastic bodies per one side of the belt.

Referring to FIG. 6, the joining of the first layer fold over of continuous sheet 93CS and the first layer of continuous sheets 92CS may be effected by the combination of adhesive applied on the second group of elastic bodies 96SC and a waist-fold adhesive WFA, and optionally the chassis-to-belt adhesive CTBA. The waist-fold adhesive WFA may have a dimension in the machine direction which at least covers the length in which the second group of elastic bodies 96SC are left intermittently unjoined. This assures the secure joining of the second group of elastic bodies 96SC between the first layer fold over of continuous sheet 93CS and the first layer of continuous sheets 92CS. Referring to FIG. 5, the chassis-to-belt adhesive CTBA and waist-fold adhesive WFA may be applied concurrently. This simplifies the adhesive applying step of parts, and contributes in shortening the overall assembling time. Application of the chassis-to-belt adhesive CTBA and waist-fold adhesive WFA may precede the step of joining the second group of elastic bodies 96SC to the first layer of continuous sheet 92CS. This enables covering the second group of elastic bodies 96SC with the first layer fold over of continuous sheets 93CS immediately after adhesive material is applied.

The thus obtained assembly is then folded at the middle point in the cross machine direction, seamed at the edges of the planned transverse edges of the article, and then finally cut to obtain a wearable article.

This application is a continuation of PCT Application No. PCT/US2017/057829, filed on Oct. 23, 2017, the entirety of which is incorporated by reference herein.

This application is a continuation-in-part of PCT Application No. PCT/CN2016/107182, filed on Nov. 25, 2016, the entirety of which is incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Further, every numerical range given throughout this specification includes every narrower numerical range that falls within such broader numerical range.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of manufacturing a wearable article assembled by a front elastic belt, a back elastic belt, and a center chassis, the center chassis having a front waist region and a back waist region separated from each other by a crotch region, and having a longitudinal axis and a lateral axis; a proximal direction closer to the longitudinal center of the article and a distal direction farther from the longitudinal center of the article; the method comprising steps of:
    advancing a first layer of continuous sheet having a first surface in a machine direction, and defining a width in a cross direction;
    advancing a second layer of discrete sheet having a first surface in the machine direction, the second layer of discrete sheet being a repetition of discrete sheets discontinuous in the machine direction having a smaller width than the first layer of continuous sheet;
    advancing a first group of elastic bodies in the machine direction in a stretched state, wherein all of the first group of elastic bodies are intermittently directly joined to the first surface of the first layer of continuous sheet and the first surface of the second layer of discrete sheet;
    directly joining the first surface of the first layer of continuous sheet and the first surface of the second layer of discrete sheet;
    advancing a second group of elastic bodies in the machine direction in a stretched state, wherein the second group of elastic bodies are directly joined to the first surface of the first layer of continuous sheets in regions outward of the second layer of discrete sheet in the width direction, wherein the second group of elastic bodies are intermittently directly joined to the first surface of the first layer of continuous sheet, wherein a portion planned for the center chassis to overlay the second group of elastic bodies are left unjoined;
    directly joining the center chassis with the first layer of continuous sheet overlapping regions in which the first group of elastic bodies are not directly joined to the first surface of the first layer of continuous sheets; and
    folding the first layer of continuous sheet to form a first layer fold over of continuous sheet, and directly joining the first layer of continuous sheet and the first layer fold over of continuous sheet, wherein the first layer fold over of continuous sheet overlaps all of the second group of elastic bodies, and at least partially overlaps the center chassis and the second layer of discrete sheet.

2. The method of claim 1, wherein the second layer of discrete continuous sheet and the center chassis have an overlap of at least about 5 mm in the machine direction.

3. The method of claim 1, wherein the center chassis at least overlaps the discrete sheet at least part a width direction of the second layer.

4. The method of claim 1, wherein any elastic body joined between the first layer of continuous sheet and the second layer of discrete sheet are at least about 5 mm away from a cross direction edge of the second layer of discrete sheet.

5. The method of claim 1, wherein the first surface of the first layer of continuous sheet and the first surface of the second layer of discrete sheet are directly joined along a periphery of a region which is planned to become a proximal edge of the front elastic belt or the back elastic belt.

6. The method of claim 1, further comprising steps of:
applying a chassis-to-belt adhesive for joining the center chassis with the first layer of continuous sheet overlapping regions where the first group of elastic bodies are not joined to the first surface of the first layer of continuous sheet; and
applying a waist-fold adhesive for joining the first layer of continuous sheet and the first layer fold over of continuous sheet; and
wherein the chassis-to-belt adhesive and the waist-fold adhesive are applied concurrently.

7. The method of claim 6, wherein the chassis-to-belt adhesive is applied beyond a width of the center chassis in the cross direction.

8. The method of claim 7, wherein the chassis-to-belt adhesive is applied in a dimension shorter than a length of the center chassis in the machine direction.

9. The method of claim 6, wherein the step of applying of the chassis-to-belt adhesive and waist-fold adhesive precedes the step of joining the second group of elastic bodies to the first layer of continuous sheet.

10. The method of claim 1, wherein at least one of the first group of elastic bodies are deactivated in regions in which the first group of elastic bodies are not directly joined to the first layer of continuous sheet.

11. The method of claim 10, wherein at least one of the first group of elastic bodies are not deactivated.

12. The method of claim 1, further comprising steps of:
applying ultrasound to join the first elastics to the first surface of the first layer of continuous sheet and the first surface of the second layer of discrete sheet; and
applying ultrasound to join the first surface of the first layer of continuous sheet and the first surface of the second layer of discrete sheet.

13. The method of claim 1, wherein a longitudinal edge of the center chassis is from about 10 mm to about 90 mm away from a belt distal edge.

14. The method of claim 1, wherein the center chassis comprises an outer cover layer at a garment-facing surface of the article and a backsheet attached to a body-facing surface of the outer cover layer; wherein a longitudinal length of the outer cover layer is longer than a longitudinal length of the crotch region and shorter than a longitudinal length of the backsheet, an area on the front elastic belt or the back elastic belt where the outer cover layer is present forming a transitional region, wherein a longitudinal length of the transitional region is no more than 10 mm.

15. A method of manufacturing a wearable article assembled by a front elastic belt, a back elastic belt, and a center chassis, the center chassis having a front waist region and a back waist region separated from each other by a crotch region, and having a longitudinal axis and a lateral axis; a proximal direction closer to the longitudinal center of the article and a distal direction farther from the longitudinal center of the article; the method comprising steps of:
advancing a first layer of continuous sheet having a first surface in a machine direction, and defining a width in a cross direction;
advancing a second layer of discrete sheet having a first surface in the machine direction, the second layer of discrete sheet being a repetition of discrete sheets discontinuous in the machine direction having a smaller width than the first layer of continuous sheet;
advancing a first group of elastic bodies in the machine direction in a stretched state, wherein all of the first group of elastic bodies are intermittently directly joined to the first surface of the first layer of continuous sheet and the first surface of the second layer of discrete sheet, wherein at least one of the first group of elastic bodies are deactivated in regions in which the first group of elastic bodies are not directly joined to the first layer of continuous sheet, and wherein at least one of the first group of elastic bodies are not deactivated;
directly joining the first surface of the first layer of continuous sheet and the first surface of the second layer of discrete sheet;
advancing a second group of elastic bodies in the machine direction in a stretched state, wherein the second group of elastic bodies are directly joined to the first surface of the first layer of continuous sheets in regions outward of the second layer of discrete sheet in the width direction;
directly joining the center chassis with the first layer of continuous sheet overlapping regions in which the first group of elastic bodies are not directly joined to the first surface of the first layer of continuous sheets; and
folding the first layer of continuous sheet to form a first layer fold over of continuous sheet, and directly joining the first layer of continuous sheet and the first layer fold over of continuous sheet, wherein the first layer fold over of continuous sheet overlaps all of the second group of elastic bodies, and at least partially overlaps the center chassis and the second layer of discrete sheet.

16. The method of claim 15, wherein the second layer of discrete sheet and the center chassis have an overlap of at least about 5 mm in the machine direction.

17. The method of claim 15, wherein the center chassis at least overlaps the discrete sheet at least part a width direction of the second layer.

18. The method of claim 15, wherein any elastic body joined between the first layer of continuous sheet and the second layer of discrete sheet are at least about 5 mm away from a cross direction edge of the second layer of discrete sheet.

19. The method of claim 15, further comprising steps of:
applying a chassis-to-belt adhesive for joining the center chassis with the first layer of continuous sheet overlapping regions where the first group of elastic bodies are not joined to the first surface of the first layer of continuous sheet; and
applying a waist-fold adhesive for joining the first layer of continuous sheet and the first layer fold over of continuous sheet; and wherein the chassis-to-belt adhesive and the waist-fold adhesive are applied concurrently.

* * * * *